United States Patent [19]

Berges

[11] 4,057,631

[45] Nov. 8, 1977

[54] 7-(α-SUBSTITUTED PHENYLACETAMIDO)-3-(1-CARBOXYMETHYLTHIOETHYLTETRAZOLYL-5-THIOMETHYL)-3-CEPHEM-4-CARBOXYLIC ACIDS

[75] Inventor: David A. Berges, Wayne, Pa.

[73] Assignee: SmithKline Corporation, Philadelphia, Pa.

[21] Appl. No.: 719,751

[22] Filed: Sept. 2, 1976

[51] Int. Cl.$^2$ .................. C07D 501/36; A61K 31/545
[52] U.S. Cl. ...................................... 424/246; 544/27; 544/26
[58] Field of Search ...................... 260/243 C; 424/246

[56] References Cited

U.S. PATENT DOCUMENTS 3,989,694   11/1976   Berges .............................. 260/243 C

*Primary Examiner*—Nicholas S. Rizzo
*Attorney, Agent, or Firm*—William H. Edgerton

[57] ABSTRACT

New semisynthetic cephalosporins characterized by having structures with a 1-carboxymethylthioethyltetrazolyl-5-thiomethyl group at position 3. Exemplary is the antibacterially effective 7-D-mandelamido-3-(1-carboxymethylthioethyltetrazolyl-5-thiomethyl)-3-cephem-4-carboxylic acid disodium salt.

6 Claims, No Drawings

7-(α-SUBSTITUTED PHENYLACETAMIDO)-3-(1-CARBOXYMETHYL-THIOETHYLTETRAZOLYL-5-THIOMETHYL)-3-CEPHEM-4-CARBOXYLIC ACIDS

This invention relates to a new series of cephalosporin compunds having antibacterial activity and to intermediates useful for preparing them. The structures of the new compounds are characterized by having at the 3-position a tetrazolylthiomethyl group having a carboxyalkylthioalkyl substituent.

Exemplary of the compounds of this invention are those represented by the following structural formula:

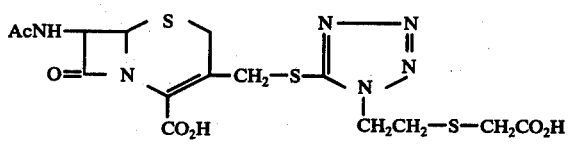

I in which Ac represents a pharmaceutically acceptable acyl group known to be of utility as a substituent on the 7-amino group in the structures of known or prior art cephalosporins or on the 6-amino group in the structures of known or prior art penicillins.

Representative acyl substituents are:

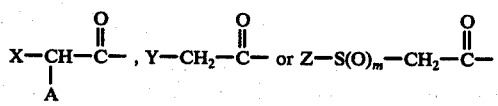

wherein:
X is thienyl, furyl, phenyl or phenyl monosubstituted with hydroxy, hydroxymethyl, formamido or ureido;
A is $NH_2$, OH, COOH, $SO_3H$, formyloxy or, when the α-C— hydrogen is absent, methoxyimino;
Y is cyano, sydnone, pyridone, thienyl, phenoxy, phenyl or tetrazolyl;
Z is methyl, trifluoromethyl, trifluoroethyl, pyridyl or cyanomethyl; and
m is zero to two.

Each of the three partial structures above represents a subgeneric group of this invention.

Representative 7-acylamino substituents of the compounds of Formula I are listed below:

α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
syn-2-methoxyimino-2-α-furylacetamido
4-pyridylthioacetamido Others may be found in Cephalosporins and Penicillins, Flynn, Academic Press, 1972; U.S. Pat. Nos. 2,721,196 and 3,953,424; Belgian Pat. No. 832,725; German Pat. Nos. 2,127,285 and 2,406,165.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such ester derivatives are included within the scope of this invention.

Also covered in this invention are the pharmaceutically acceptable, nontoxic derivatives of the compounds of Formula I from which they derive utility: the salts, as stated above easily split ester or ether derivatives of either a carboxy or hydroxy function, amide derivatives at an amino radical such as in a 7-glycylamino group as the furyl, pyranyl, oxolanyl or oxiranylcarbonylamides (Belgian Pat. No. 835,295), the solvates such as hydrates or alcoholates. As examples of these one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine.

Other known cephalosporin modifications can be made by known synthetic procedures such as introduction of an α-methoxy group at position 7, preferably at the stage of the 7-aminocephalosporanic acid reactants disclosed below (IV), prior to N-acylation. Optical isomers are also possible such as with the mandeloyl or glycyl substituents at 7. The D-forms of these series are preferred.

The compounds of this invention are most conveniently prepared by a displacement of the acetoxy group of a known 7-acylaminocephalosporanic acid (II) by 1-carboxymethylthioethyltetrazole-5-thiol (III). Alternatively the displacement can be run on 7-aminocephalosporanic acid to give 7-amino-3-(1-carboxymethylthioethyltetrazolyl-5-thiomethyl)-3-cepham-4carboxylic acid (IV) which may then be N-acylated as known to the art. Suitable protective groups may be used in either method as is known to the art (see "Protective Groups in Organic Chemistry", J. F. W. McOmie, Plenum Press, 1973, Chapters 2 and 3 for use of amino, carboxy, sulfo or hydroxyl protective groups). For example the t-butyl (for COOH) or t-butoxycarbonyl (for $NH_2$) groups are easily removed by treatment with trifluoroacetic acid.

The compounds of Formula I have antibacterial activity against either Gram positive or Gram negative bacteria with minimum inhibitory concentrations (MIC's) in vitro from 0.4 to 100 μg/ml. Test results for 7-D-mandelamido-3-(1-carboxymethylthioethyltetrazolyl-5-thiomethyl)-3-cephem-4-carboxylic acid, disodium salt, hydrate (A) are:

|  | A | Cefazolin | Cephalothin |
|---|---|---|---|
| S. aureus HH 127 | 1.6 | 0.4 | 0.4 |
| S. aureus SK 23390 | 0.4 | 0.2 | 0.1 |
| S. aureus villaluz SK 70390 | 12.5 | 25 | 3.1 |
| Strep. Faecalis HH 34358 | 25 | 3.1 | 12.5 |
| E. coli SK 12140 | 1.6 | 1.6 | 6.3 |
| E. coli HH 33779 | 6.3 | 3.1 | 25 |

-continued

| | A | Cefazolin | Cephalothin |
|---|---|---|---|
| Kleb. pneumo. SK 4200 | 1.6 | 3.1 | 12.5 |
| Kleb. pneumo. SK 1200 | 0.8 | 3.1 | 12.5 |
| Salmonella ATCC 12176 | 12.5 | 6.3 | 12.5 |
| Pseudo. sp. HH 63 | >200 | >200 | >200 |
| Serra. marc. ATCC 13880 | 100 | >200 | >200 |
| Proteus morgani 179 | 3.1 | 50 | >200 |
| Entero. aerog. ATCC 13048 | 6.3 | 12.5 | 100 |
| Entero. cloacae HH 31254 | 0.8 | 6.3 | 25 |

Compound A gave an $ED_{50}$ in mice of 1.56 mg/kg against E. coli and 0.46 mg/kg against Kleb. pneumo. (s.c.); 34 mg/kg against E. coli and 21.5 mg/kg against Kleb. pneumo. (p.o.). Cephalexin gives comparable values of 2.5; 15.7; 25; 10 respectively. Extended testing in vitro (μg/ml) of Compound A against a spectrum of strains of several prominent bacteria gave the following ranges: Indole-pos. Proteus (0.1–200); Proteus mir. (0.2–0.8); Klebsiella (0.2–100); Staphylococcus (0.4–6.3); E. coli (0.4–1.6); Serratia (12.5–>200) and Enterobacter (0.8–>200).

Pharmaceutical compositions having antibacterial activity which comprise a pharmaceutical carrier containing an active but nontoxic quantity of a compound of Formula I as well as methods of combatting bacterial infections by administering such a composition to an infected animal or human host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula I are formulated and administered in the same manner as other prior art cephalosporins. The dosage regimen comprises administration, preferably by injection, of an active but nontoxic quantity of a compound of Formula I selected from the dosage unit range of from about 100 mg to 500 mg with the total daily dosage regimen being from about 400 mg to 6 g. The precise dosages are dependent upon the age and weight of the subject and on the susceptibility of the infection being treated. These can be determined by those skilled in the art based on the data disclosed herein compared with that available to the art attained with the known cephalosporins outlined hereinbefore.

The following examples illustrate the invention but are not to be construed as limiting the scope thereof. Temperatures are in degrees Centigrade (° C.) unless otherwise stated.

EXAMPLE 1

A solution of 21.0 g (100 mmol) of bromoethylamine hydrobromide in 40 ml of water was added to a mixture of 8 ml (10.6 g, 110 mmol) of thioglycolic acid in 200 ml of 10% sodium hydroxide solution. The mixture was stirred at room temperature overnight. The mixture was neutralized with 6N hydrochloric acid then passed over an IR 120 HCP ion exchange column eluting first with water then 0.5N ammonium hydroxide. The product containing fractions (by t.l.c.) were pooled and evaporated to dryness to give 14.0 g of semicrystalline solid which was taken through water and alcohol to give 11.4 g (84%) of crystalline aminoethylthioacetic acid.

A mixture of 23.3 ml (17 g, 0.168 mol) of triethylamine, 11.3 g (83.7 mmol) of the amino acid and 70 ml of 95% ethanol was allowed to stand for 45 minutes when 5.5 ml (6 g, 87 mmol) of carbon disulfide was added. After 40 minutes 5.23 ml (11.9 g, 84 mmol) of methyl iodide was added followed by stirring overnight. The mixture was filtered. The filtrate was evaporated. The oily residue was dissolved in 100 ml of water. The cooled solution was made acid with 55.5 ml of 1.5N hydrochloric acid. The mixture was extracted with ether. The extracts were dried and evaporated to give the dithiocarbamate derivative.

A mixture of 30 g (83 mmol) of this product, 3.2 g (80 mmol) of sodium hydroxide and 5.2 g (80 mmol) of sodium azide in 100 ml of water was stirred at room temperature for 15 minutes, heated at reflux for 1 hour and cooled to room temperature overnight. The reaction mixture, after heating for 1 more hour, was extracted with 200 ml of ethyl acetate.

The aqueous layer was cooled and mixed with 55 ml (165 mmol) of 3N hydrochloric acid. The desired product was extracted with ethyl acetate. The dried combined extracts were evaporated to give an oil which was dried over high vacuum to give 18.3 g of slowly crystallizing solid. Trituration with chloroform gave 13.3 g (75%) of 1-carboxymethylthioethyltetrazole-5-thiol. This intermediate compound and its alkali metal salts such as its sodium and potassium salts are part of this invention.

The thiol (2.20 g, 10 mmol) was added slowly to a solution of 1.68 g (20 mmol) of sodium bicarbonate in 40 ml of water. Then 3.0 g (7 mmol) of 7-D-mandelamidocephalosporanic acid, sodium salt was added. The mixture (pH = 6.4) was heated at 80° C. for 3 hours then cooled at 4° C. overnight. The solution was again heated for 1½ hours at 80° C. The reaction was demonstrated by t.l.c. to be essentially complete so the mixture was filtered. The filtrate was added to a column of XAD-7 resin (a crosslinked polymer of acrylic esters with an average pore diameter of 80A). Elution with water and evaporation of the eluate gave a foamy brown product. Precipitation from aqueous methanol by addition of isopropanol gave the desired product, 7-D-mandelamido-3-(1-carboxymethylthioethyltetrazolyl-5-thiomethyl)-3-cepham-4-carboxylic acid as the disodium salt 3.5 hydrate.

Anal. calculated: C, 37.43; H, 4.03; N, 12.47. Found: C, 37.93; H, 3.55; N, 12.25.

EXAMPLE 2

A mixture of 5.22 g (10.0 mmol) of 7-(D-α-t-butoxycarbonylamino-4-hydroxyphenylacetamido)cephalosporanic acid and an excess (15.0 mmol) of 1-carboxymethylthioethyltetrazole-5-thiol in 75 ml or pH 6.4 phosphate buffer solution is treated with sufficient sodium bicarbonate to give a pH of 6.4. The mixture is heated at 70° for 3 hours, cooled, acidified with dilute hydrochloric acid to pH 2 and extracted with ethyl acetate. The extracts are dried and evaporated to give a residue which is then chromatographed on silica gel with chloroform-isopropanol-formic acid as eluant to give the t-boc derivative of the desired compound. This derivative is stirred at 25° C. with 25 ml of trifluoroacetic acid and 25 ml of 1,3-dimethoxybenzene for 2 hours. The mixture is evaporated to dryness, ether added to the residue and the precipitated salt collected. This is dissolved in water and the solution treated with Amberlite IR-45 ion exchange resin. Lyophilizing the supernatent liquid gives 7-(D-α-amino-4-hydroxyphenylacetamido)-3-(1-carboxymethylthioethyltetrazolyl-5-thiomethyl)-3-cepham-4-carboxylic acid. Similar treatment of the t-boc derivatives of the DL-7-(α-aminophenylacetamidocephalosporanic acid gives the corresponding 7-(α-aminophenylacetamido)-3-(1-carboxymethylthioethyltetrazolyl-5-thiomethyl)-3-cephem-4-carboxylic acid.

EXAMPLE 3

A mixture of an excess (12.2 mmol) of 1-carboxymethylthioethyltetrazole-5-thiol, 32.5 mmol of sodium bicarbonate and 8.1 mmol of 7-trifluoromethylthioacetamidocephalosporanic acid in 50 ml of water is stirred at 70° for 5 hours. The mixture is cooled and passed over XAD-2 resin with water and methanol as eluants. The methanol eluants are evaporated to dryness to give a residue which is dissolved in a small amount of water and lyophilized to give 7-trifluoromethylthioacetamido-3-(1-carboxymethylthioethyltetrazolyl-5-thiomethyl)-3-cephem-4-carboxylic acid disodium salt. Substituting 7-(2-thienyl)-acetamidocephalosporanic acid gives 7-(2-thienyl)-acetamido-3-(1-carboxymethylthioethyltetrazolyl-5-thiomethyl)-3-cephem-4-carboxylic acid disodium salt.

Stoichiometric quantities of cephalosporanic acids having the individual 7-acylamino substituent listed hereabove may be substituted in Examples 1-3 with variations which will be obvious to those skilled in this art.

EXAMPLE 4

An injectable pharmaceutical composition is formed by adding sterile saline solution (2 ml) to 350 mg of the product of Example 1. This material is injected parenterally four times daily to a human patient infected with susceptible bacteria. Other compounds of this invention may be similarly used.

What is claimed is:

1. A compound or its nontoxic alkali metal salts, said compound being of the structure:

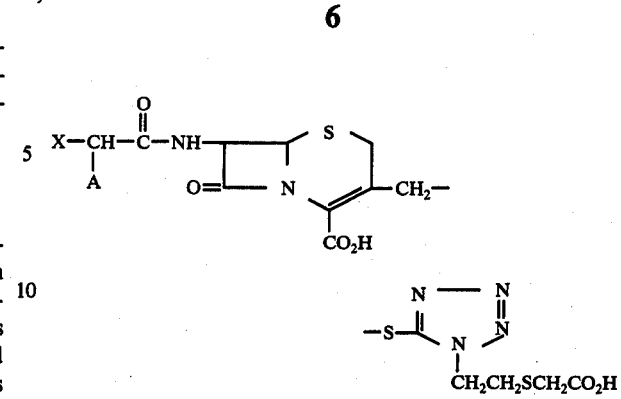

in which:
X is thienyl, furyl, phenyl or phenyl monosubstituted with hydroxy, hydroxymethyl, formamido or ureido; and
A is $NH_2$, OH, COOH, $SO_3H$, formyloxy or, when the α-C- hydrogen is absent, methoxyimino.

2. The compound of claim 1 being 7-D-mandelamido-3-(1-carboxymethylthioethyltetrazolyl-5-thiomethyl)-3-cephem-4-carboxylic acid.

3. The compound of claim 1 being 7-D-mandelamido-3-(1-carboxymethylthioethyltetrazolyl-5-thiomethyl)-3-cephem-4-carboxylic acid disodium salt.

4. The compound of claim 1 being 7-(D-α-amino-4-hydroxyphenylacetamido)-3-(1-carboxymethylthioethyltetrazolyl-5-thiomethyl)-3-cephem-4-carboxylic acid.

5. A pharmaceutical composition having antibacterial activity comprising a nontoxic antibacterially effective quantity of a compound as claimed in claim 1 and a pharmaceutically acceptable carrier therefor.

6. A method of treating bacterial infections comprising administering internally to an infected or susceptible human subject an antibacterially effective but nontoxic dose of a compound as claimed in claim 1.

* * * * *